United States Patent
Bennett et al.

(10) Patent No.: US 9,943,236 B2
(45) Date of Patent: Apr. 17, 2018

(54) METHODS FOR GUIDING HEART FAILURE DECOMPENSATION THERAPY

(75) Inventors: Tommy D. Bennett, Shoreview, MN (US); Yong K. Cho, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 1469 days.

(21) Appl. No.: 12/571,091

(22) Filed: Sep. 30, 2009

(65) Prior Publication Data

US 2011/0077616 A1 Mar. 31, 2011

(51) Int. Cl.
| | | |
|---|---|---|
| *A61B 5/0215* | (2006.01) | |
| *A61M 5/142* | (2006.01) | |
| *A61M 5/172* | (2006.01) | |
| *A61N 1/365* | (2006.01) | |
| *A61N 1/372* | (2006.01) | |

(52) U.S. Cl.
CPC ....... *A61B 5/0215* (2013.01); *A61M 5/14276* (2013.01); *A61M 5/1723* (2013.01); *A61N 1/36521* (2013.01); *A61N 1/36564* (2013.01); *A61M 2205/054* (2013.01); *A61M 2210/125* (2013.01); *A61N 1/3655* (2013.01); *A61N 1/36557* (2013.01); *A61N 1/37282* (2013.01)

(58) Field of Classification Search
CPC .............. A61B 5/0215; A61N 1/36564; A61N 1/36521; A61M 5/1723
USPC ...................................... 604/65–67, 503–505
See application file for complete search history.

(56) References Cited

U.S. PATENT DOCUMENTS

| | | |
|---|---|---|
| 4,995,268 A | 2/1991 | Ash |
| 5,368,040 A | 11/1994 | Carney |
| 5,876,353 A | 3/1999 | Riff |
| 6,287,608 B1 | 11/2001 | Levin |
| 6,438,408 B1 | 8/2002 | Mulligan |
| 6,512,949 B1 | 1/2003 | Combs |
| 6,595,927 B2 | 7/2003 | Pitts-Crick |
| 7,004,924 B1* | 2/2006 | Brugger et al. ............. 604/6.13 |
| 7,029,456 B2* | 4/2006 | Ware et al. .................... 604/131 |
| 7,177,681 B2 | 2/2007 | Zhu |
| 7,191,000 B2 | 3/2007 | Zhu |
| 2007/0073168 A1* | 3/2007 | Zhang et al. ................. 600/483 |
| 2007/0293463 A1 | 6/2007 | Dittrich |

FOREIGN PATENT DOCUMENTS

WO 2008014078 6/2007

OTHER PUBLICATIONS

Ohlsson et al, Monitoring of pulmonary arterial diastolic pressure through a right ventricular pressure transducer, Mar. 1995, Journal of Cardiac Failure, vol. 1, Issue 2, pp. 161-168.*

* cited by examiner

*Primary Examiner* — Bradley Osinski

(57) ABSTRACT

An implantable medical device system and associated method for use in guiding an acute decompensated heart failure therapy set an optimal fluid status measurement level. A physiological sensor signal sensed by an implantable medical device is used to compute the fluid status measurement. A target rate of change of the fluid status measurement is computed for guiding the therapy.

17 Claims, 5 Drawing Sheets

METHODS FOR GUIDING HEART FAILURE DECOMPENSATION THERAPY

TECHNICAL FIELD

The disclosure relates generally to implantable medical devices and, in particular, to an implantable medical device (IMD) and associated method for guiding a heart failure therapy.

BACKGROUND

Implantable medical devices are available for monitoring physiological signals for use in diagnosing and managing cardiac disease. For example, implantable hemodynamic monitors can monitor heart rhythm, blood pressure and thoracic fluid status for tracking the status of heart failure patients. In the early stages of heart failure, compensatory mechanisms occur in response to the heart's inability to pump a sufficient amount of blood. One compensatory response is an increase in filling pressure of the heart. The increased filling pressure increases the volume of blood in the heart, allowing the heart to more efficiently eject a larger volume of blood on each heart beat. Increased filling pressure and other compensatory mechanisms can initially occur without overt heart failure symptoms.

The mechanisms that initially compensate for insufficient cardiac output, however, lead to heart failure decompensation as the heart continues to weaken. The weakened heart can no longer pump effectively causing increased filling pressure to lead to chest congestion (thoracic edema) and heart dilation, which further compromises the heart's pumping function. The patient begins the "vicious cycle" of heart failure which generally leads to hospitalization.

Typically, therapy for a patient hospitalized for acute decompensated heart failure (ADHF) includes early introduction of intravenous infusion of diuretics or vasodilators to clear fluid retained by the patient. This therapy can be highly effective in reducing ADHF symptoms rapidly, but overdiuresis can occur if the intravenous infusion of drugs is delivered too long or at too high of a dosage. Since there is a lag in time between reaching an optimal fluid volume status and the alleviation of symptoms, determining the optimal parameters for controlling the intravenous infusion therapy remains a challenge to clinicians. Overdiuresis may require fluid to be administered to the patient to increase the patient's fluid volume status. Removing and adding fluid can pose additional burden on the kidneys, which may already be compromised due to renal insufficiency in the heart failure patient. At other times, the fluid removed may not be sufficient to achieve a desired result. A need remains, therefore, for apparatus and methods for guiding ADHF therapy.

DETAILED DESCRIPTION

Figure 1:
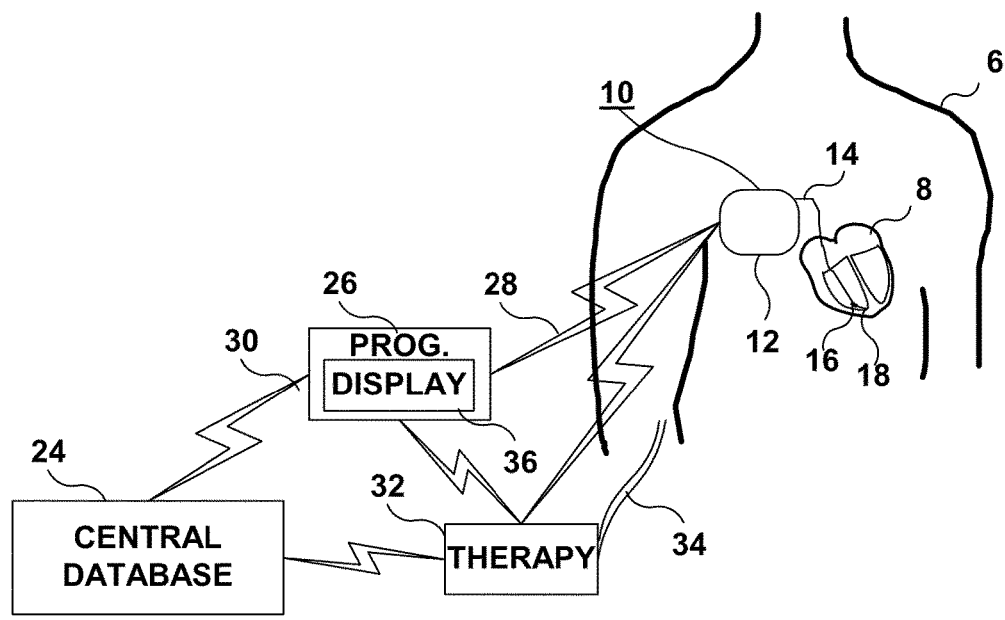
FIG. 1 is a schematic diagram of an implantable medical device (IMD) coupled to a lead positioned within a heart in a patient's body.

In the following description, references are made to illustrative embodiments. It is understood that other embodiments may be utilized without departing from the scope of the invention. For purposes of clarity, the same reference numbers are used in the drawings to identify similar elements.

As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Methods and associated apparatus described herein generally relate to controlling a therapy for treating ADHF. ADHF generally refers to a worsened state of heart failure resulting in hospitalization, an emergency room visit, or an urgent care visit and requiring therapeutic intervention above and beyond the chronic medications and/or IMD-delivered therapies that the patient may be receiving to manage chronic heart failure. Typically the ADHF therapy is delivered in a hospital with close medical supervision although ADHF therapies may also be delivered in a clinic or even at home. An "ADHF therapy" as referred to herein is a therapy that is typically administered over a period of approximately one week or less, and may include therapies that are managed over a period of several hours, several days, or in some cases several weeks. An ADHF therapy is generally more aggressive, e.g. higher dosage, than chronic therapies that are delivered over periods of weeks, months or years. ADHF therapy often includes infusion of medications such as diuretics and/or vasodilators at a dosage that is typically higher than a longer-term, daily dosage that might be taken by the patient.

While one application of the methods described herein relates to the treatment of ADHF, it is recognized that the methods may be used to guide other therapies used for treating patients that may be hypervolemic, hypovolemic, or edemic due to any associated medical condition. Other conditions that may adversely affect a patient's fluid status include renal failure and hyponatremia.

FIG. 1 is a schematic diagram of an implantable medical device (IMD) 10 coupled to a lead 14 positioned within a heart 8 in a patient's body 6. IMD 10 is capable of monitoring at least one physiological signal from which variables useful in monitoring a patient's fluid status can be derived. IMD 10 may or may not be provided with therapy delivery capabilities. IMD 10 may correspond to a variety of implantable medical devices including a cardiac pacemaker, implantable cardioverter defibrillator, implantable hemodynamic monitor, a drug pump, a neurostimulator or the like. Accordingly, IMD 10 may be coupled to additional leads and/or catheters operatively positioned relative to the patient's heart 8 or other body tissues for deploying stimulating/sensing electrodes, other physiological sensors, and/or drug delivery ports. While lead 14 is shown terminated within the right ventricle of the patient's heart, it is recognized that lead 14 may be configured as a transvenous lead that extends into other heart chambers or blood vessels for positioning electrodes and/or physiological sensors in a desired location.

In one embodiment, IMD 10 corresponds to an implantable hemodynamic monitor capable of sensing and recording ECG signals, intracardiac right ventricular pressure signals, and transthoracic impedance signals. IMD 10 may store the sensed signals and further derives fluid status measurements from the sensed signals for monitoring the fluid volume status of the patient. ECG signals are sensed using one or more electrodes 18 carried by lead 14 or using alternative electrodes (not shown) incorporated on the hermetically-sealed housing 12 of IMD 10. Housing 12 encloses circuitry (not shown in FIG. 1) included in IMD 10 for controlling and performing device functions and processing sensed signals.

An electrode 18 carried by lead 14 is used with the IMD housing 12 for measuring a transthoracic impedance for use in monitoring fluid status. As used herein, "transthoracic" impedance refers to any impedance measurement across a portion of the thorax, including across a portion of the heart, lungs and pulmonary vascular bed. In alternative embodiments, one or more lead-based electrodes and/or one or more subcutaneously placed electrodes, incorporated on IMD housing 12 or carried by a subcutaneously extending lead, may be used to measure transthoracic impedance across a portion of the thoracic cavity, heart and/or lungs for use in deriving a variable useful in monitoring fluid status.

Transthoracic impedance decreases with heart failure decompensation as fluid accumulates in the chest and the heart dilates due to elevated right heart filling pressures and insufficient cardiac ejection. Electrical impedance decreases as the fluid in the chest increases. As such, transthoracic impedance measurements may be used in deriving a fluid status measurement useful in controlling a therapy administered to an ADHF patient.

As used herein, a "fluid status measurement" is a measurement or index derived from a physiological sensor signal and is correlated to the blood volume of the patient or edemic state of the patient. As such a worsening fluid status measurement is a measurement that corresponds to increased fluid retention by the patient corresponding to hypervolemia or edema. A stable fluid status measurement generally corresponds to an optivolemic state of the patient. A hypervolemic or hypovolemic (overdiuresed) state of the patient corresponds to a fluid status measurement that crosses an optivolemic level of the fluid status measurement, which may be an increasing or decreasing change in the fluid status measurement depending on the particular measurement being used. For example, a fluid status measurement based on intraventricular pressure would increase with worsening edema (hypervolemia) and would decrease in a state of overdiuresis (hypovolemia). A fluid status measurement based on transthoracic impedance may decrease with increasing edema (hypervolemia) and increase with overdiuresis (hypovolemia).

Lead 14 is further provided with a pressure sensor 16. Pressure sensor 16 is used for monitoring pressure within the right ventricle (RV) for use in deriving pressure-related fluid status measurements. The RV pressure signal can be used to determine an estimated pulmonary artery diastolic (ePAD), pressure which increases during heart failure decompensation. While ePAD pressure is one useful variable that can be derived from a RV pressure signal, numerous other pressure-related variables may be useful in monitoring a fluid status. Furthermore, pressure signals obtained at other locations in the heart or vasculature may be used for deriving a fluid status measurement. Other pressure measurements such as pulmonary artery pressure, left atrial pressure, and/or central venous pressures can also be used for deriving pressure-related fluid status measurements.

IMD 10 is capable of bidirectional communication with an external device 26 via telemetry link 28. Device 26 may be embodied as a programmer or home monitor used to program the operating mode and various operational variables of IMD 10 and/or interrogate IMD 10 to retrieve data stored by IMD 10. Stored data may include data related to IMD function determined through automated self-diagnostic tests as well as physiological data acquired by IMD 10 using pressure sensor 16 and electrode(s) 18.

External device 26 is further shown in communication with a central database 24 via communication link 30, which may be a wireless or hardwired link. Programming data and interrogation data may be transmitted via link 30. Central database 24 may be a centralized computer, web-based or other networked database used by a clinician for remote monitoring and management of patient 6. Various methods described herein and executed for determining the fluid status of a patient using one or more physiological signals sensed by IMD 10 may be implemented in one or more of the IMD system components shown in FIG. 1, namely in the IMD 10, external device 26 and/or central database 24, and may include any combination of hardware, firmware and/or software. External device 26 may be embodied as a clinic-based programmer having full IMD programming and interrogation functionality or a home-based monitor having interrogation and perhaps limited programming functionality and used for remote patient monitoring. It is recognized that other external devices, such as other physiological monitoring devices or other types of programming devices, may be used in conjunction with IMD 10 and incorporate portions of the methods described herein.

Therapy delivery device 32 is used to administer an acute therapy for treating ADHF. Therapy delivery device 32 may be embodied as an infusion pump coupled to a catheter 34 for administering intravenous fluids to the patient, such as intravenous diuretics or vasodilators. In some embodiments, therapy delivery device 32 is enabled for telemetric communication with IMD 10, programmer or monitor 26 and/or central database 24. Therapy delivery device 32 may receive data, such as therapy delivery control parameters, fluid status data for use by therapy delivery device 32 to set delivery control parameters, or notifications relating to the patient's fluid status. In this way, automated control of therapy delivery may be achieved using fluid status measurements obtained by IMD 10.

In other embodiments, therapy delivery device 32 is manually adjusted in response to fluid status measurements and notifications provided by IMD 10, which may be transmitted for viewing on an external display 36 by a nurse or clinician, which may be provided on programmer/monitor 26 or alternatively associated with central database 24. When therapy delivery device 32 is enabled for communication with IMD 10, programmer 26 or central database 24, therapy delivery device 32 may include a display (not shown) for displaying data received from the IMD system relating to the patient's fluid status.

Figure 2:
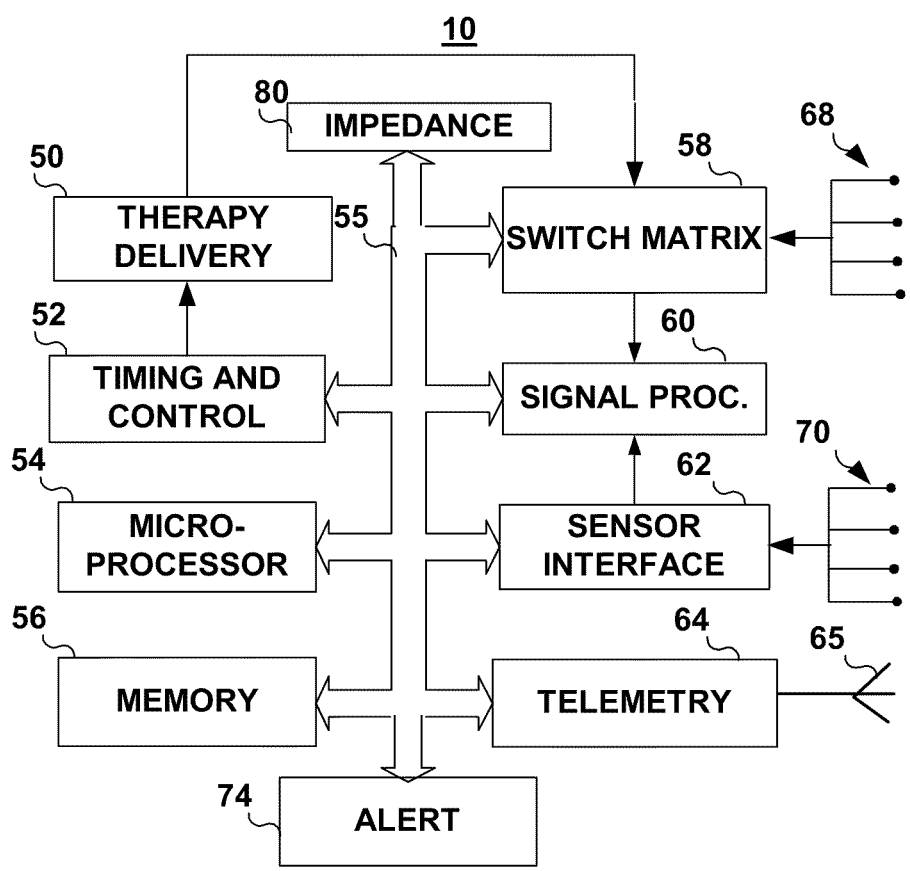
FIG. 2 is a functional block diagram of one embodiment of an IMD.

FIG. 2 is a functional block diagram of one embodiment of IMD 10. IMD 10 generally includes timing and control circuitry 52 and a control unit that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy in response to determining a need for therapy, e.g., based on sensed physiological signals. Therapy delivery module 50 may provide drug delivery therapies or electrical stimulation therapies, such as cardiac pacing or anti-arrhythmia therapies. Therapies are delivered by module 50 under the control of timing and control circuitry 52.

IMD 10 can be implemented as an interrupt-driven device in which case various computations, algorithms, or other device functions are executed upon generation of an interrupt signal.

Therapy delivery module 50 is typically coupled to two or more electrodes 68 via an optional switch matrix 58. Switch matrix 58 may be used for selecting which electrodes and corresponding polarities are used for delivering electrical stimulation pulses. Electrodes 68 may correspond to any electrodes incorporated in IMD housing 12 or other lead-based electrodes, including electrode(s) 18 carried by lead 14 (shown in FIG. 1).

Electrodes 68 are also used for receiving cardiac electrical signals through any unipolar or bipolar sensing configuration. Cardiac electrical signals may be monitored for use in diagnosing or managing a patient condition or may be used for determining when a therapy is needed and controlling the timing and delivery of the therapy. When used for sensing, electrodes 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias.

As discussed above, IMD 10 may be configured to measure impedance signals for deriving a thoracic fluid status. As such, selected electrodes 68 are coupled to impedance measuring module 80 for providing an impedance measurement drive signal along an excitation path. The voltage is then measured across the measuring electrodes allowing the impedance across the measurement path to be computed from the known drive signal and the measured voltage. Impedance measurement methods and associated apparatus are generally disclosed in PCT Publication WO 2008/014078 (Stylos), incorporated herein by reference in its entirety.

IMD 10 is additionally coupled to one or more sensors 70 used to monitor physiological signals. Physiological sensors 70 include pressure sensor 16 as shown in FIG. 1 and may further include accelerometers, flow sensors, blood chemistry sensors, activity sensors, posture sensors, oxygen sensors, or other physiological sensors used in conjunction with implantable medical devices. Physiological sensors may be carried by leads extending from IMD 10, incorporated in or on the IMD housing 12, or embodied as wireless sensors in telemetric communication with IMD 10.

Sensor signals are received by a sensor interface 62 which may provide initial amplification, filtering, rectification, or other signal conditioning. Sensor signals may then be provided to signal processing circuitry 60 for analog to digital conversion, averaging, integration, peak detection or other signal processing required for a particular application to derive desired signal features. Microprocessor 54 receives the processed sensor signals for detecting physiological events or conditions. In particular, signals from pressure sensor 16 are processed by signal processor 60 and/or microprocessor 54 for deriving a fluid status measurement from a pressure signal.

A fluid status monitoring algorithm may be stored in memory 56 and executed by microprocessor 54 with input received from electrodes 68, physiological sensors 70, processor 60 and impedance measuring module 80. Microprocessor 54 in conjunction with memory 56 may operate as a control unit for executing software-implemented algorithms for monitoring fluid status using an impedance variable and/or a pressure variable derived by processor 60, impedance module 80, and/or by microprocessor 54 using sensed signals. The algorithms may be stored in memory 56 and retrieved therefrom by microprocessor 54 as needed. In alternative embodiments, functionality described herein may be implemented using dedicated hardware and/or firmware.

Fluid status data may be stored for use in diagnosing or monitoring the patient, determining the need for delivering an IMD therapy under control of the operating system, and for use in controlling a therapy for treating ADHF as will be described in detail below. Memory 56 may store a variety of programmed parameter values that are used by microprocessor 54. Memory 56 may also be used for storing data compiled from sensed physiological signals and/or relating to device operating history for telemetry out on receipt of a retrieval or interrogation instruction.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit such as programmer 26 as shown in FIG. 1.

Alert module 74 generates patient or clinician notifications in response to detecting various patient-related or device-related conditions. A notification may be an audible sound or a message transmitted via telemetry 64 to an external device. A notification may be generated by module 74 in response to fluid status measurements determined by IMD 10. In particular, a notification may be generated by IMD 10 when fluid status measurements monitored by IMD 10 deviate from a target fluid status level or target rate of change of the fluid status measurement.

Methods described herein are generally indicated as being executed by the IMD 10 however, as previously mentioned, any of the functionality described herein may be implemented across the components of a medical device and therapy delivery system, for example the system shown in FIG. 1, including at least an IMD for gathering fluid status measurements and a therapy delivery device for administering a therapy for treating ADHF.

Illustrative embodiments described in detail below relate primarily to an acute therapy, which may last several hours or days, delivered in a hospital or clinic under medical supervision. While such therapies are generally administered using external therapy delivery apparatus, such as an infusion pump, methods described herein for controlling an ADHF therapy may be used to control a therapy delivered by IMD 10, or another IMD implanted and in wired or telemetric communication with IMD 10. For example, if IMD 10 is embodied as an implantable drug pump, increased dosages of diuretics or vasodilators may be delivered using IMD 10 instead of an external infusion pump.

Figure 3:
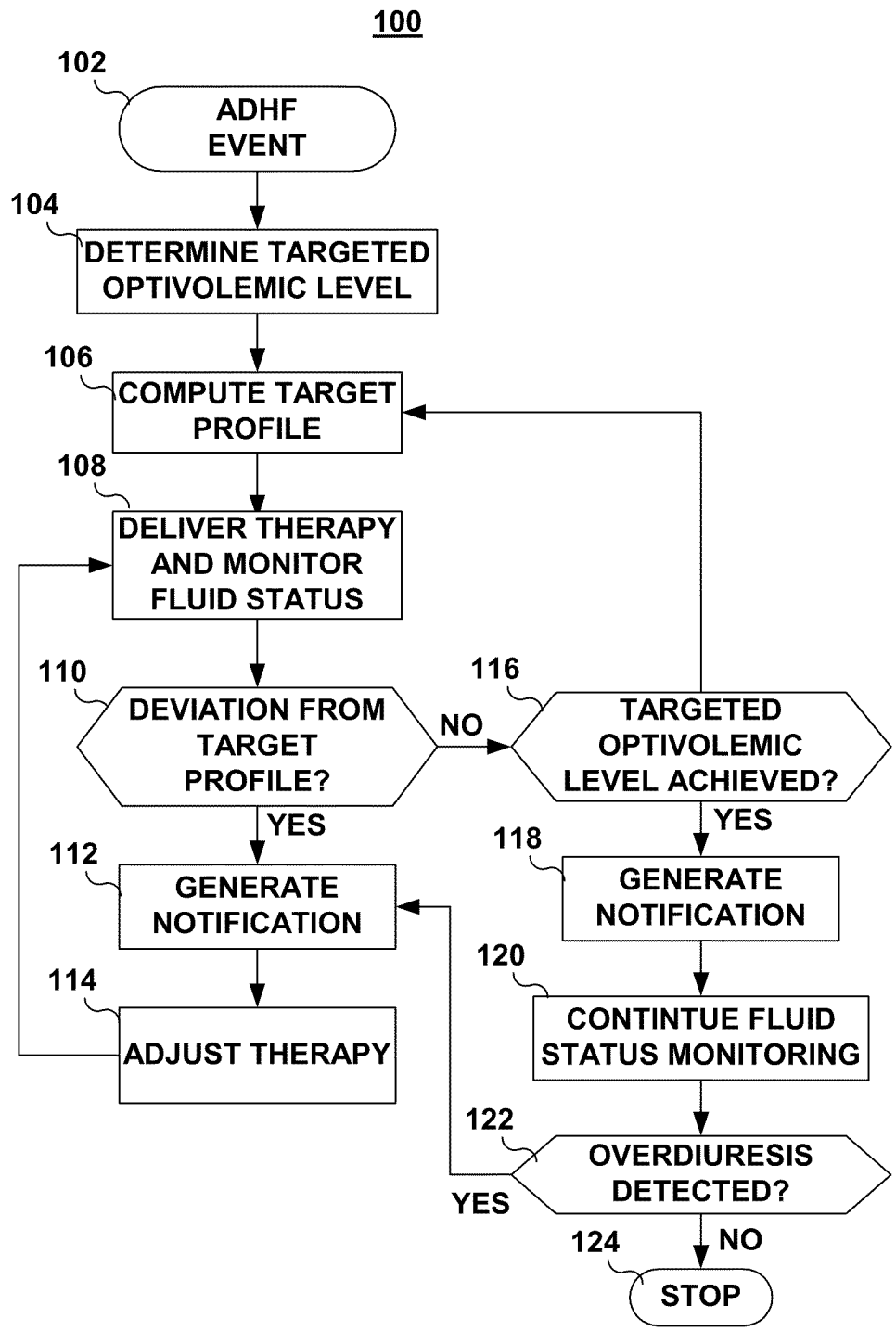
FIG. 3 is a flow chart of a method for controlling a therapy for treating ADHF.

FIG. 3 is a flow chart 100 of one embodiment of a method for controlling a therapy for treating ADHF. Flow chart 100 is intended to illustrate the functional operation of the device, and should not be construed as reflective of a specific form of software or hardware necessary to practice the embodiments described herein. It is believed that the particular form of software will be determined primarily by the particular system architecture employed in the device and by the particular detection and therapy delivery methodologies employed by the device. Providing software to accomplish the described functionality in the context of any modern implantable medical device system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102, an ADHF event occurs requiring therapeutic intervention to stabilize the patient and alleviate heart failure symptoms. An ADHF event will typically be a hospitalization due to overt symptoms associated with heart failure decompensation. A physician decision is made at block 102 to administer an ADHF therapy to quickly stabilize the patient.

At block 104 a targeted optivolemic level is determined. The targeted optivolemic level is a level of a physiological sensor derived measurement of the patient's fluid status determined by the IMD. In one embodiment, the optivolemic level may be defined as a level of an intracardiac blood pressure, ePAD pressure, or other pressure measurement. In other embodiments, the optivolemic level may be defined as a level of a transthoracic impedance measurement. In still other embodiments, the optivolemic level may be determined as a combination of two or more fluid status measurements obtained by an IMD using an implantable physiological sensor, such as a combination of an intracardiac pressure measurement and a transthoracic impedance measurement.

The targeted optivolemic level may be determined by a clinician and programmed into an external programmer, central database or other IMD system component as a user-entered value for one or more fluid status measurements monitored by the IMD. An optivolemic level is a level of the fluid status measurement at which the patient is expected to be hemodynamically stable with reduced heart failure symptoms. The patient may still be hemodynamically compromised due to the heart failure condition however intracardiac pressures and fluid status are expected to be stable and not adversely increasing or decreasing once the optivolemic level is reached.

The optivolemic level may be based on known clinical data for a patient population, the patient's own history of ADHF events, or the patient's own history of a given fluid status measurement. For example, a patient's own history of ADHF events may be stored by the IMD or by the central database and the level of the fluid status measurement at the time of prior ADHF events may be used in selecting a fluid status measurement level that is expected to be stable for the given patient.

Alternatively, the targeted optivolemic level may be computed automatically from stored fluid status measurement data. For example, an optivolemic level may be computed from all stored fluid status measurement data acquired for a given patient to date or from all data acquired during a selected time period preceding the ADHF event. A statistical analysis of stored data may be performed to determine an optivolemic level as a fluid status measurement level or range that the patient is at for the greatest amount of time. Alternatively, a percentile of the sensor data distribution may be determined such as the twentieth percentile of an intracardiac pressure measurement or a range, e.g. between tenth and twentieth percentile. This percentile may be an upper or lower percentile depending on the measurement being used. For example, for a pressure measurement the lower twentieth percentile might be used since pressure increases with worsened fluid status. For an impedance measurement, an upper percentile or percentile range would be used since impedance decreases with a worsening fluid status.

At block 106, a targeted fluid status profile may be computed using the current fluid status measurement(s), the targeted optivolemic level and an expected duration of the ADHF therapy or a total time period over which the optivolemic level is desired to be reached. The target profile is a time-based slope or curve of the fluid status measurement, i.e. a target rate of change of the fluid status measurement, as it is brought from a worsened level at the time of the ADHF event to the optivolemic level. The target profile, also referred to herein as a "target rate of change", is used to guide the ADHF therapy to bring the fluid status measurement down to the optivolemic level in a controlled manner without causing too rapid of a change, which may result in overdiuresis.

At block 108, the ADHF therapy is delivered and the fluid status is monitored by the IMD using sensor-derived measurements and comparing the measurements to the targeted optivolemic level and targeted profile. If the fluid status measurements plotted over time, i.e. an actual rate of change of the fluid status measurements, do not match the target profile, a notification may be generated at block 112. Matching of the actual rate of change to the target profile may be determined as a deviation from the target rate of change by less than a predefined acceptable range or percentage from the target profile. By matching a target rate of change, a drop in the fluid status measurement that occurs too quickly, potentially leading to overdiuresis, is avoided. In contrast, methods that delivery a therapy to restore an optivolemic level of a fluid status measurement which do not take into account the rate of change of the fluid status measurement, during or after cessation of the therapy, can inadvertently result in a hypovolemic or overdiuresed condition.

Figure 4:
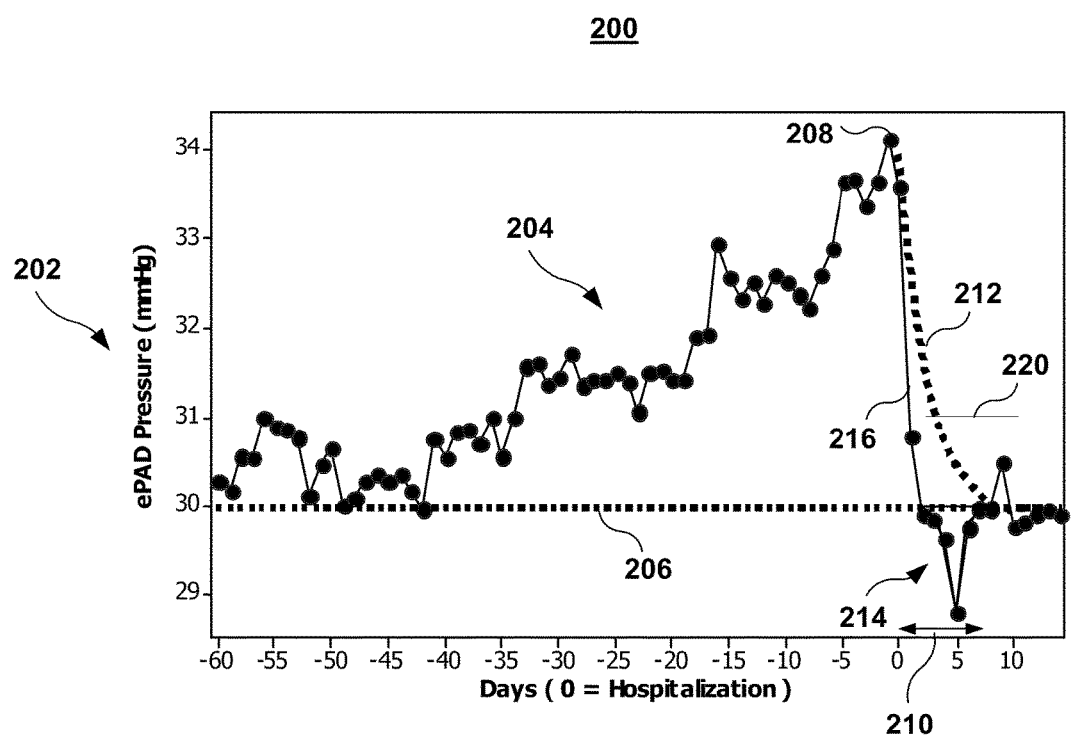
FIG. 4 is a time-based plot of a fluid status measurement monitored by an IMD.

FIG. 4 is a time-based plot 200 of a fluid status measurement monitored by an IMD. In this example, the fluid status measurement is the cumulative sum of an ePAD pressure derived from an intraventricular pressure measurement. Briefly, ePAD pressure is determined as the RV pressure occurring at an inflection point in the intraventricular RV pressure waveform. The time of this inflection point, which corresponds to the time of pulmonary valve opening can be found by finding the time of the peak of the first time derivative of the RV pressure signal. Methods for deriving ePAD pressure are generally described in U.S. Pat. No. 5,368,040 (Carney), incorporated herein by reference in its entirety. A cumulative sum (CUSUM P) of the differences between an ePAD pressure value and a measured baseline can be determined as a monitored fluid status measurement. Increases in CUSUM P indicate the presence of increasing pressure changes consistent with increased filling pressure since ePAD pressure is an estimate of left atrial pressure.

At day 0, the patient is hospitalized for ADHF after an increasing trend 204 in ePAD for approximately 45 days. An optivolemic level 206 is determined, as described previously, based on clinician input or automatically determined based on patient event history (i.e. hospitalizations, appearance of symptoms, etc.) and/or statistical analysis of stored fluid status measurement data. A targeted fluid status profile 212 is computed using the ePAD level 308 at the time of hospitalization (therapy initiation), the targeted ePAD optivolemic level 206, and a desired time period 210 over which the targeted optivolemic level is to be reached. In this example, the time period 210 is approximately one week but may vary depending on individual patient condition and clinician preference from anywhere between a few hours to a few weeks.

Depending on the type of ADHF therapy being delivered, the therapy may be delivered over the entire time period 210 during which the fluid status measurement is brought down to an optivolemic level 206. In other cases, the therapy may be delivered for an initial period of time and then the fluid status measurement monitored. The therapy may or may not be restarted during time period 210 depending on the course of the fluid status measurement relative to the targeted profile 212.

The time period 210 may correspond to a planned duration of the ADHF therapy or may be longer than the therapy duration. For example, a patient may be given intravenous medication on the first day after hospitalization to quickly remove fluid and stabilize the patient symptoms. Since the removal of water retained in the tissues will lag water removal from the blood, the fluid status will continue to fall after a therapy is discontinued. The fluid status continues to be monitored relative to the targeted profile 212 and optivolemic level 206 until the optivolemic level 206 is reached. It is contemplated that physiological signals other than pressure and impedance, such as temperature, blood oxygen saturation, or the like, may be utilized in monitoring the patient's condition with targeted and actual levels of other physiological variables being tracked in a similar manner as described herein.

In this way, during and after the ADHF therapy, the fluid status can be monitored to allow intervention to be taken if the fluid status begins to fall too rapidly or is falling too slowly relative to the targeted profile. Medications or other therapies may be adjusted. By monitoring the fluid status measurements relative to a targeted profile 212, overshoot of the optivolemic level can be avoided.

As shown in FIG. 4, in some cases, aggressive ADHF therapy delivered upon hospitalization can quickly bring down the patient's hypervolemic condition as shown by an actual ePAD profile 216. However, when the fluid volume is reduced too quickly, overdiuresis 214 can occur as shown by the ePAD pressure overshooting (falling below) the optivolemic level 206. One goal of managing ADHF therapy based on IMD fluid status measurements is to avoid overdiuresis of the patient. When the actual fluid status profile 216 deviates by more than a predefined range, for example five or ten percent, from the targeted profile 212, a notification may be generated and/or a therapy may be adjusted.

In some embodiments, instead of comparing the fluid status measurements to a targeted profile 212, the fluid status measurements may be compared to the targeted optivolemic level 206. When the targeted level is reached or is closely approached, for example by identifying a crossing of an intermediate threshold 220, a notification may be generated such that a therapy may be slowed or the patient may be more closely monitored. The therapy can be adjusted or terminated manually in response to a notification or automatically if the IMD system is in communication with the ADHF therapy delivery device. It is contemplated that multiple intermediate thresholds 220 may be defined to monitor the progress of the therapy. Multiple thresholds may be selected to have increasing resolution as the optivolemic level 206 is more closely approached.

Furthermore, it is contemplated that a fluid status measurement determined using IMD sensor signals may be computed and reported more frequently as the optivolemic level 206 is approached. For example, a daily fluid status measurement may be provided during normal patient monitoring. During an ADHF therapy or upon reaching an intermediate threshold 220, the fluid status measurement may be determined and reported more frequently, for example every eight hours.

Referring again to FIG. 3, if a deviation from a target profile is detected at block 110, a notification may be generated at block 112. The ADHF therapy may be adjusted at block 114, manually or automatically. The therapy and monitoring continues at block 108 until the optivolemic level is reached as determined at block 116. It is recognized that an adjustment at block 114 may be terminating the therapy.

A notification may be generated at block 118 to alert the clinician that the optivolemic level has been achieved. The method may then be terminated at block 120. A notification generated at block 112 or 118 may be an audible alarm, a visual display, an electronic message sent to a personal computer or hand held device, a phone call placed to a cell phone, or the like.

In some embodiments, fluid status monitoring may continue for a desired interval of time at block 120 to ensure that a stable state has been reached and that the optivolemic level is maintained for a predetermined interval of time. If overdiuresis is detected at block 122 based on a fluid status measurement less than the targeted optivolemic level, a notification may again be generated at block 112 and appropriate therapeutic intervention taken at block 114.

Figure 5:
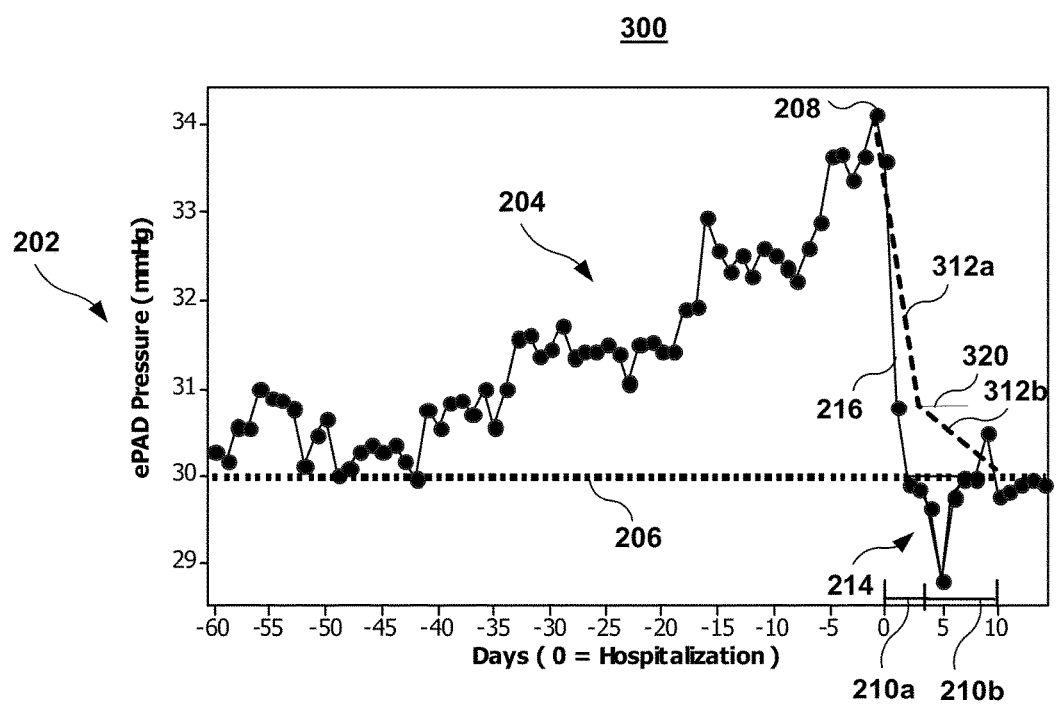
FIG. 5 is time-based plot of a fluid status measurement illustrating an alternative method for controlling an ADHF therapy.

FIG. 5 is a time-based plot 300 of a fluid status measurement illustrating an alternative method for controlling an ADHF therapy. In FIG. 5, a dual slope targeted profile 312a and 312b, referred to collectively as 312, is computed. In FIG. 5, the same drawing elements as shown in FIG. 4 are identified by identical reference numerals. Briefly, the ePAD pressure 202 shows an increasing trend 204 up to a maximum measurement 208 at hospitalization on Day 0. A therapy is initiated and results in an actual fluid status profile 216 that rapidly falls and overshoots the targeted optivolemic level 206.

In order to prevent overdiuresis, a targeted profile 312 is computed to manage and guide the ADHF therapy. The targeted profile 312 may be linear or non-linear, such as an exponentially decreasing profile as shown in FIG. 4. In the example of FIG. 5, the targeted profile 312 is computed to have dual slope. As such, the targeted profile 312 is computed to have a first slope 312a between the initial ePAD pressure 208 and a first target level 320 to be achieved within a first time interval 210a and a second slope 312b between the first target level 320 and the optivolemic level 206 achieved during a second time interval 210b. In this way, the fluid status may be managed to rapidly improve over an initial, typically shorter time interval 210a and then adjust more slowly down to the optivolemic level 206 to prevent overdiuresis.

Thus, methods and associated apparatus for managing ADHF therapy have been presented in the foregoing description with reference to specific embodiments. It is appreciated that various modifications to the referenced embodiments may be made without departing from the scope of the invention as set forth in the following claims.

The invention claimed is:

1. An implantable medical device method, comprising:
   setting an optimal level of a fluid status measurement of a volemic state of a patient;
   sensing a physiological signal;
   computing from the sensor signal the fluid status measurement;
   administering a therapy;

establishing a target profile of a time-based curve of the fluid status measurement using an expected time period of the therapy, the fluid status measurement and the optimal level;

determining an actual profile of a time-based curve of the fluid status measurement during the therapy administration;

comparing the actual profile to the target profile; and generating a notification if the actual profile of the fluid status measurement subsequent to initiating the administered therapy does not match the target profile.

2. The method of claim 1 further comprising displaying the computed fluid status measurement over time.

3. The method of claim 1 wherein setting the optimal fluid status measurement level comprises:

storing a fluid status measurement corresponding to acute decompensated heart failure events; and computing the optimal fluid status measurement level in response to the stored fluid status measurement.

4. The method of claim 1 wherein setting the optimal fluid status measurement level comprises using a distribution of previously computed fluid status measurements.

5. The method of claim 1 wherein sensing the physiological sensor signal comprises sensing one of an impedance signal and a blood pressure signal.

6. The method of claim 1 wherein establishing the target profile of the fluid status measurement comprises establishing a duration of the therapy and a target change in the fluid status measurement during the duration of the therapy.

7. The method of claim 1 further comprising automatically adjusting the therapy administration in response to exceeding the target rate.

8. The method of claim 1 further comprising adjusting the therapy administration to maintain the actual profile of the fluid status measurement within a range of the target profile.

9. The method of claim 8 wherein adjusting the therapy administration to maintain the actual profile of the time-based curve of the fluid status measurement comprises adjusting the therapy to prevent the fluid status measurement from falling below the optimal level.

10. The method of claim 1 wherein the therapy comprises intravenous infusion of one of a diuretic and a vasodilator.

11. The method of claim 1 wherein computing the target profile comprises computing a first target rate of change over a first time period and second target rate of change over a second time period, the second target rate of change being different than the first target rate of change.

12. The method of claim 11 wherein the second target rate of change is slower than the first target rate of change and further comprising adjusting the therapy to maintain the actual rate of change within a range of the second target rate of change after the computed fluid status measurement reaches an intermediate fluid status measurement greater than the optimal fluid status measurement level.

13. The method of claim 1 wherein the fluid status measurement is a measurement or index derived from an implantable physiological sensor signal and is correlated to a blood volume of a patient.

14. The method of claim 1, wherein the fluid status measurement is an estimated pulmonary artery diastolic pressure.

15. An implantable medical device method, comprising:
setting an optimal level of a fluid status measurement of a volemic state of a patient;
sensing a physiological sensor signal;
computing from the sensor signal the fluid status measurement;
administering a therapy;
establishing a target profile of a time-based curve of the fluid status measurement using an expected time period of the therapy, the fluid status measurement and the optimal level;
determining an actual profile of a time-based curve of the fluid status measurement during the therapy administration; and
comparing the actual profile to the target profile,
wherein setting the optimal fluid status measurement level comprises:
storing the fluid status measurement corresponding to acute decompensated heart failure events; and
computing the optimal fluid status measurement level in response to the stored fluid status measurement.

16. A method, comprising:
setting an optimal level of a fluid status measurement of a volemic state of a patient;
sensing a physiological sensor signal;
computing the fluid status measurement from the sensor signal;
administering a therapy; and
establishing a target profile of a time-based curve of the fluid status measurement using an expected time period of the therapy, the fluid status measurement and the optimal level,
determining an actual profile of a time-based curve of the fluid status measurement during the therapy administration;
comparing the actual profile to the target profile;
wherein setting the optimal fluid status measurement level comprises using a distribution of previously computed fluid status measurements.

17. An implantable medical device method, comprising:
setting an optimal level of a fluid status measurement of a volemic state of a patient in an implantable medical device;
sensing a physiological sensor signal from an implantable sensor;
computing from the sensor signal the fluid status measurement;
administering a therapy through the implantable medical device;
establishing a target profile of a time-based curve of the fluid status measurement using an expected time period of the therapy, the fluid status measurement and the optimal level;
determining an actual profile of a time-based curve of the fluid status measurement during the therapy administration; and
comparing the actual profile to the target profile;
wherein sensing the physiological sensor signal comprises sensing one of an impedance signal and a blood pressure signal.

* * * * *